US005104974A

United States Patent [19]

Sick et al.

[11] Patent Number: 5,104,974

[45] Date of Patent: Apr. 14, 1992

[54] *BACILLUS THURINGIENSIS* COLEOPTERAN-ACTIVE TOXIN

[75] Inventors: August J. Sick; Thomas E. Gilroy, both of San Diego, Calif.

[73] Assignee: Mycogen Corporation, San Diego, Calif.

[21] Appl. No.: 435,101

[22] Filed: Nov. 9, 1989

Related U.S. Application Data

[62] Division of Ser. No. 164,044, Mar. 4, 1988, Pat. No. 4,996,155.

[51] Int. Cl.[5] ...................... C07K 13/00; C12N 15/32; A01N 63/00

[52] U.S. Cl. ................................... 530/350; 530/825; 435/691; 435/71.1; 435/91; 435/172.1; 435/172.3; 435/320.1; 435/252.3; 435/254; 435/822; 435/911; 435/946; 536/27; 935/6; 935/9; 935/22; 935/59; 935/60; 935/64; 935/66; 935/68; 935/72; 935/73; 935/74; 935/75

[58] Field of Search ............... 530/350, 825; 435/69.1, 435/71.1, 91, 172.1, 172.3, 320.1, 252.3, 254, 822, 911, 946; 424/93; 935/6, 9, 22, 59, 60, 64, 66, 68, 72, 73, 74, 75; 536/27

[56] References Cited

U.S. PATENT DOCUMENTS

| | | | |
|---|---|---|---|
| 4,448,885 | 5/1984 | Schnepf et al. | 435/253 |
| 4,467,036 | 8/1984 | Schnepf et al. | 435/317 |
| 4,771,131 | 9/1988 | Hamstadt et al. | 536/27 |

FOREIGN PATENT DOCUMENTS 0202739 11/1986 European Pat. Off. .

OTHER PUBLICATIONS

Thorne et al., 1986, *J. Bacteriol.*, 166/31:801–811.

Schnepf, H. E. and Whitely, H. R. (1981) "Cloning and Expression of the *Bacillus thuringiensis* Crystal Protein Gene in *Escherichia coli*," Proc. Natl. Acad. Sci. U.S.A. 78: 2893–2897.

*Primary Examiner*—Richard C. Peet

*Attorney, Agent, or Firm*—Saliwanchik & Saliwanchik

[57] ABSTRACT

A novel B.t. toxin gene encoding a protein toxic to coleopteran insects has been cloned from a novel coleopteran-active *B. thuringiensis* microbe. The DNA encoding the B.t. toxin can be used to transform various prokaryotic and eukaryotic microbes to express the B.t. toxin. These recombinant microbes can be used to control coleopteran insects in various environments.

1 Claim, 3 Drawing Sheets

FIGURE 1-1

| | | | | | 5 | | | | | 10 | | | | | 15 |
|---|---|---|---|---|---|---|---|---|---|---|---|---|---|---|---|
| 1 | Met | Asn | Pro | Asn | Asn | Arg | Ser | Glu | Tyr | Asp | Thr | Ile | Lys | Val | Thr |
| 16 | Pro | Asn | Ser | Glu | Leu | Pro | Thr | Asn | His | Asn | Gln | Tyr | Pro | Leu | Ala |
| 31 | Asp | Asn | Pro | Asn | Ser | Thr | Leu | Glu | Glu | Leu | Asn | Tyr | Lys | Glu | Phe |
| 46 | Leu | Arg | Met | Thr | Ala | Asp | Asn | Ser | Thr | Glu | Val | Leu | Asp | Ser | Ser |
| 61 | Thr | Val | Lys | Asp | Ala | Val | Gly | Thr | Gly | Ile | Ser | Val | Val | Gly | Gln |
| 76 | Ile | Leu | Gly | Val | Val | Gly | Val | Pro | Phe | Ala | Gly | Ala | Leu | Thr | Ser |
| 91 | Phe | Tyr | Gln | Ser | Phe | Leu | Asn | Ala | Ile | Trp | Pro | Ser | Asp | Ala | Asp |
| 106 | Pro | Trp | Lys | Ala | Phe | Met | Ala | Gln | Val | Glu | Val | Leu | Ile | Asp | Lys |
| 121 | Lys | Ile | Glu | Glu | Tyr | Ala | Lys | Ser | Lys | Ala | Leu | Ala | Glu | Leu | Gln |
| 136 | Gly | Leu | Gln | Asn | Asn | Phe | Glu | Asp | Tyr | Val | Asn | Ala | Leu | Asp | Ser |
| 151 | Trp | Lys | Lys | Ala | Pro | Val | Asn | Leu | Arg | Ser | Arg | Arg | Ser | Gln | Asp |
| 166 | Arg | Ile | Arg | Glu | Leu | Phe | Ser | Gln | Ala | Glu | Ser | His | Phe | Arg | Asn |
| 181 | Ser | Met | Pro | Ser | Phe | Ala | Val | Ser | Lys | Phe | Glu | Val | Leu | Phe | Leu |
| 196 | Pro | Thr | Tyr | Ala | Gln | Ala | Ala | Asn | Thr | His | Leu | Leu | Leu | Leu | Lys |
| 211 | Asp | Ala | Gln | Val | Phe | Gly | Glu | Glu | Trp | Gly | Tyr | Ser | Ser | Glu | Asp |

FIGURE 1-2

| | | | | | 5 | | | | | 10 | | | | | 15 |
|---|---|---|---|---|---|---|---|---|---|---|---|---|---|---|---|
| 226 | Ile | Ala | Glu | Phe | Tyr | Gln | Arg | Gln | Leu | Lys | Leu | Thr | Gln | Gln | Tyr |
| 241 | Thr | Asp | His | Cys | Val | Asn | Trp | Tyr | Asn | Val | Gly | Leu | Asn | Ser | Leu |
| 256 | Arg | Gly | Ser | Thr | Tyr | Asp | Ala | Trp | Val | Lys | Phe | Asn | Arg | Phe | Arg |
| 271 | Arg | Glu | Met | Thr | Leu | Thr | Val | Leu | Asp | Leu | Ile | Val | Leu | Phe | Pro |
| 286 | Phe | Tyr | Asp | Val | Arg | Leu | Tyr | Ser | Lys | Gly | Val | Lys | Thr | Glu | Leu |
| 301 | Thr | Arg | Asp | Ile | Phe | Thr | Asp | Pro | Ile | Phe | Thr | Leu | Asn | Ala | Leu |
| 316 | Gln | Glu | Tyr | Gly | Pro | Thr | Phe | Ser | Ser | Ile | Glu | Asn | Ser | Ile | Arg |
| 331 | Lys | Pro | His | Leu | Phe | Asp | Tyr | Leu | Arg | Gly | Ile | Glu | Phe | His | Thr |
| 346 | Arg | Leu | Arg | Pro | Gly | Tyr | Ser | Gly | Lys | Asp | Ser | Phe | Asn | Tyr | Trp |
| 361 | Ser | Gly | Asn | Tyr | Val | Glu | Thr | Arg | Pro | Ser | Ile | Gly | Ser | Asn | Asp |
| 376 | Thr | Ile | Thr | Ser | Pro | Phe | Tyr | Gly | Asp | Lys | Ser | Ile | Glu | Pro | Ile |
| 391 | Gln | Lys | Leu | Ser | Phe | Asp | Gly | Gln | Lys | Val | Tyr | Arg | Thr | Ile | Ala |
| 406 | Asn | Thr | Asp | Ile | Ala | Ala | Phe | Pro | Asp | Gly | Lys | Ile | Tyr | Phe | Gly |
| 421 | Val | Thr | Lys | Val | Asp | Phe | Ser | Gln | Tyr | Asp | Asp | Gln | Lys | Asn | Glu |
| 436 | Thr | Ser | Thr | Gln | Thr | Tyr | Asp | Ser | Lys | Arg | Tyr | Asn | Gly | Tyr | Leu |

FIGURE 1-3

| | | | | | 5 | | | | | 10 | | | | | 15 |
|---|---|---|---|---|---|---|---|---|---|---|---|---|---|---|---|
| 451 | Gly | Ala | Gln | Asp | Ser | Ile | Asp | Gln | Leu | Pro | Pro | Glu | Thr | Thr | Asp |
| 466 | Glu | Pro | Leu | Glu | Lys | Ala | Tyr | Ser | His | Gln | Leu | Asn | Tyr | Ala | Glu |
| 481 | Cys | Phe | Leu | Met | Gln | Asp | Arg | Arg | Gly | Thr | Ile | Pro | Phe | Phe | Thr |
| 496 | Trp | Thr | His | Arg | Ser | Val | Asp | Phe | Phe | Asn | Thr | Ile | Asp | Ala | Glu |
| 511 | Lys | Ile | Thr | Gln | Leu | Pro | Val | Val | Lys | Ala | Tyr | Ala | Leu | Ser | Ser |
| 526 | Gly | Ala | Ser | Ile | Ile | Glu | Gly | Pro | Gly | Phe | Thr | Gly | Gly | Asn | Leu |
| 541 | Leu | Phe | Leu | Lys | Glu | Ser | Ser | Asn | Ser | Ile | Ala | Lys | Phe | Lys | Val |
| 556 | Thr | Leu | Asn | Ser | Ala | Ala | Leu | Leu | Gln | Arg | Tyr | Arg | Val | Arg | Ile |
| 571 | Arg | Tyr | Ala | Ser | Thr | Thr | Asn | Leu | Arg | Leu | Phe | Val | Gln | Asn | Ser |
| 586 | Asn | Asn | Asp | Phe | Leu | Val | Ile | Tyr | Ile | Asn | Lys | Thr | Met | Asn | Ile |
| 601 | Asp | Gly | Asp | Leu | Thr | Tyr | Gln | Thr | Phe | Asp | Phe | Ala | Thr | Ser | Asn |
| 616 | Ser | Asn | Met | Gly | Phe | Ser | Gly | Asp | Thr | Asn | Asp | Phe | Ile | Ile | Gly |
| 631 | Ala | Glu | Ser | Phe | Val | Ser | Asn | Glu | Lys | Ile | Tyr | Ile | Asp | Lys | Ile |
| 646 | Glu | Phe | Ile | Pro | Val | Gln | | | | | | | | | |

*BACILLUS THURINGIENSIS* COLEOPTERAN-ACTIVE TOXIN

This is a division of application Ser. No. 164,044, filed Mar. 4, 1988, now U.S. Pat. No. 4,996,155.

BACKGROUND OF THE INVENTION

The most widely used microbial pesticides are derived from the bacterium *Bacillus thuringiensis.* This bacterial agent is used to control a wide range of leaf-eating caterpillars, Japanese beetles and mosquitos. *Bacillus thuringiensis* produces a proteinaceous paraspore or crystal which is toxic upon ingestion by a susceptible insect host. For example, *B. thuringiensis* var. kurstaki HD-1 produces a crystal called a delta toxin which is toxic to the larvae of a number of lepidopteran insects. The cloning and expression of this B.t. crystal protein gene in *Escherichia coli* has been described in the published literature (Schnepf, H. E. and Whitely, H. R. [1981] Proc. Natl. Acad. Sci. USA 78:2893–2897). U.S. Pat. Nos. 4,448,885 and 4,467,036 both disclose the expression of B.t. crystal protein in *E. coli.* European Patent Application, Publication No. 0 202 739, discloses a novel *B. thuringiensis* microbe which can be used to control coleopteran pests in various environments.

BRIEF SUMMARY OF THE INVENTION

Disclosed and claimed is a novel toxin gene toxic to coleopteran insects. This toxin gene can be transferred to suitable hosts via plasmid vector.

Specifically, the invention comprises a novel delta endotoxin gene which encodes a 74.228 kd protein which is active against coleopteran pests.

More specifically, the subject invention concerns a novel toxin gene (DNA) encoding a novel protein having activity against coleopteran insects.

Table 1 discloses the DNA encoding the novel toxin. Table 2 discloses the amino acid sequence of the novel hybrid toxin. Table 3 is a composite of Tables 1 and 2.

FIG. 1—Deduced amino acid sequence of novel toxin.

DETAILED DESCRIPTION OF THE INVENTION

The novel toxin gene of the subject invention was obtained from a novel coleopteran-active *B. thuringiensis* (B.t.) isolate designated 43F. The gene was isolated using the open reading frame (ORF) of the delta endotoxin gene from B.t. var. san diego (B.t.s.d.) as a probe. B.t.s.d. is available from the culture repository in Peoria, Ill., U.S.A., identified in detail, infra, where its accession number is NRRL B-15939. The gene was cloned on a 7.5 Kb EcoRI fragment in Lambda ZAP TM (Stratagene Cloning Systems). This cloning vehicle readily yielded the cloned gene in the plasmid BLUESCRIPT TM (Stratagene). Sequence and expression data are in agreement with an open reading frame of 1963 bp that encodes a protein of 74.228 Kd.

*B. thuringiensis* isolate 43F, NRRL B-18298, can be cultured using standard known media and fermentation techniques. Upon completion of the fermentation cycle, the bacteria can be harvested by first separating the B.t. spores and crystals from the fermentation broth by means well known in the art. The recovered B.t. spores and crystals can be formulated into a wettable powder, a liquid concentrate, granules or other formulations by the addition of surfactants, dispersants, inert carriers and other components to facilitate handling and application for particular target pests. The formulation and application procedures are all well known in the art and are used with commercial strains of *B. thuringiensis* (HD-1) active against Lepidoptera, e.g., caterpillars. B.t. isolate 43F can be used to control coleopteran pests.

Subcultures of B.t. isolate 43F and the E. coli host harboring the toxin gene of the invention, E. coli XL1-Blue (pM1,98-4) were deposited in the permanent collection of the Northern Research Laboratory, U.S. Department of Agriculture, Peoria, Ill., U.S.A. on Feb. 2, 1988, and on Jan. 15, 1988, respectively. The accession numbers are as follows:

B.t. isolate 43F-NRRL B-18298

*E. coli* XL1-Blue (pM1,98-4)-NRRL B-18291

The subject cultures have been deposited under conditions that assure that access to the cultures will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposit, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposit(s). All restrictions on the availability to the public of the subject culture deposits will be irrevocably removed upon the granting of a patent disclosing them.

The toxin gene of the subject invention can be introduced into a wide variety of microbial hosts. Expression of the toxin gene results, directly or indirectly, in the intracellular production and maintenance of the pesticide. With suitable hosts, e.g., Pseudomonas, the microbes can be applied to the situs of coleopteran insects where they will proliferate and be ingested by the insects. The result is a control of the unwanted insects. Alternatively, the microbe hosting the toxin gene can be treated under conditions that prolong the activity of the toxin produced in the cell. The treated cell then can be applied to the environment of target pest(s). The resulting product retains the toxicity of the B.t. toxin.

Where the B.t. toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera Pseudomonas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, and Alcaligenes; fungi, particularly yeast, e.g., genera Saccharomyces, Cryptococcus, Kluyveromyces, Sporobolomyces, Rhodotorula, and Aureobasidium. Of particular interest are such phytosphere bacterial species as *Pseudomonas syringae, Pseudomonas fluorescens, Serratia marcescens, Acetobacter xylinum, Agrobacterium tumefaciens, Rhodopseudomonas spheroides, Xanthomonas campestris, Rhizobium melioti, Alcaligenes entrophus,* and *Azotobacter vinlandii;* and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae,* and *Aureobasidium pollulans.* Of particular interest are the pigmented microorganisms.

A wide variety of ways are available for introducing the B.t. gene expressing the toxin into the microorganism host under conditions which allow for stable maintenance and expression of the gene. One can provide for DNA constructs which include the transcriptional and translational regulatory signals for expression of the toxin gene, the toxin gene under their regulatory control and a DNA sequence homologous with a sequence in the host organism, whereby integration will occur, and/or a replication system which is functional in the host, whereby integration or stable maintenance will occur.

The transcriptional initiation signals will include a promoter and a transcriptional initiation start site. In some instances, it may be desirable to provide for regulative expression of the toxin, where expression of the toxin will only occur after release into the environment. This can be achieved with operators or a region binding to an activator or enhancers, which are capable of induction upon a change in the physical or chemical environment of the microorganisms. For example, a temperature sensitive regulatory region may be employed, where the organisms may be grown up in the laboratory without expression of a toxin, but upon release into the environment, expression would begin. Other techniques may employ a specific nutrient medium in the laboratory, which inhibits the expression of the toxin, where the nutrient medium in the environment would allow for expression of the toxin. For translational initiation, a ribosomal binding site and an initiation codon will be present.

Various manipulations may be employed for enhancing the expression of the messenger, particularly by using an active promoter, as well as by employing sequences, which enhance the stability of the messenger RNA. The initiation and translational termination region will involve stop codon(s), a terminator region, and optionally, a polyadenylation signal.

In the direction of transcription, namely in the 5′ to 3′ direction of the coding or sense sequence, the construct will involve the transcriptional regulatory region, if any, and the promoter, where the regulatory region may be either 5′ or 3′ of the promoter, the ribosomal binding site, the initiation codon, the structural gene having an open reading frame in phase with the initiation codon, the stop codon(s), the polyadenylation signal sequence, if any, and the terminator region. This sequence as a double strand may be used by itself for transformation of a microorganism host, but will usually be included with a DNA sequence involving a marker, where the second DNA sequence may be joined to the toxin expression construct during introduction of the DNA into the host.

By a marker is intended a structural gene which provides for selection of those hosts which have been modified or transformed. The marker will normally provide for selective advantage, for example, providing for biocide resistance, e.g., resistance to antibiotics or heavy metals; complementation, so as to provide prototropy to an auxotrophic host, or the like. Preferably, complementation is employed, so that the modified host may not only be selected, but may also be competitive in the field. One or more markers may be employed in the development of the constructs, as well as for modifying the host. The organisms may be further modified by providing for a competitive advantage against other wild-type microorganisms in the field. For example, genes expressing metal chelating agents, e.g., sidercphores, may be introduced into the host along with the structural gene expressing the toxin. In this manner, the enhanced expression of a siderophore may provide for a competitive advantage for the toxin-producing host, so that it may effectively compete with the wild-type microorganisms and stably occupy a niche in the environment.

Where no functional replication system is present, the construct will also include a sequence of at least 50 basepairs (bp), preferably at least about 100 bp, and usually not more than about 1000 bp of a sequence homologous with a sequence in the host. In this way, the probability of legitimate recombination is enhanced, so that the gene will be integrated into the host and stably maintained by the host. Desirably, the toxin gene will be in close proximity to the gene providing for complementation as well as the gene providing for the competitive advantage. Therefore, in the event that a toxin gene is lost, the resulting organism will be likely to also lose the complementing gene and/or the gene providing for the competitive advantage, so that it will be unable to compete in the environment with the gene retaining the intact construct.

A large number of transcriptional regulatory regions are available from a wide variety of microorganism hosts, such as bacteria, bacteriophage, cyanobacteria, algae, fungi, and the like. Various transcriptional regulatory regions include the regions associated with the trp gene, lac gene, gal gene, the lambda left and right promoters, the Tac promoter, the naturally-occurring promoters associated with the toxin gene, where functional in the host. See for example, U.S. Pat. Nos. 4,332,898, 4,342,832 and 4,356,270. The termination region may be the termination region normally associated with the transcriptional initiation region or a different transcriptional initiation region, so long as the two regions are compatible and functional in the host.

Where stable episomal maintenance or integration is desired, a plasmid will be employed which has a replication system which is functional in the host. The replication system may be derived from the chromosome, an episomal element normally present in the host or a different host, or a replication system from a virus which is stable in the host. A large number of plasmids are available, such as pBR322, pACYC184, RSF1010, pR01614, and the like. See for example, Olson et al., (1982) J. Bacteriol. 150:6069, and Bagdasarian et al., (1981) Gene 16:237, and U.S. Pat. Nos. 4,356,270, 4,362,817, and 4,371,625.

The B.t. gene can be introduced between the transcriptional and translational initiation region and the transcriptional and translational termination region, so as to be under the regulatory control of the initiation region. This construct will be included in a plasmid, which will include at least one replication system, but may include more than one, where one replication system is employed for cloning during the development of the plasmid and the second replication system is necessary for functioning in the ultimate host. In addition, one or more markers may be present, which have been described previously. Where integration is desired, the plasmid will desirably include a sequence homologous with the host genome.

The transformants can be isolated in accordance with conventional ways, usually employing a selection technique, which allows for selection of the desired organism as against unmodified organisms or transferring organisms, when present. The transformants then can be tested for pesticidal activity.

Suitable host cells, where the pesticide-containing cells will be treated to prolong the activity of the toxin in the cell when the then treated cell is applied to the environment of target pest(s), may include either prokaryotes or eukaryotes, normally being limited to those cells which do not produce substances toxic to higher organisms, such as mammals. However, organisms which produce substances toxic to higher organisms could be used, where the toxin is unstable or the level of application sufficiently low as to avoid any possibility of toxicity to a mammalian host. As hosts, of particular interest will be the prokaryotes and the lower eukaryotes, such as fungi. Illustrative prokaryotes, both Gram-negative and -positive, include Enterobacteriaceae, such as Escherichia, Erwinia, Shicella, Salmonella, and Proteus; Bacillaceae; Rhizobiceae, such as Rhizobium; Spirillaceae, such as photobacterium, Zymomonas, Serratia, Aeromonas, Vibrio, Desulfovib rio, Spirillum; Lacto bacillaceae; Pseudomonadaceae, such as Pseudomonas and Acetobacter; Azotobacteraceae and Nitrobacteraceae. Among eukaryotes are fungi, such as Phycomycetes and Ascomycetes, which includes yeast, such as Saccharomyces and Schizosaccharomyces; and Basidiomycetes yeast, such as Rhodotorula, Aureobasidium, Sporobolomyces and the like.

Characteristics of particular interest in selecting a host cell for purposes of production include ease of introducing the B.t.i. gene into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; leaf affinity; lack of mammalian toxicity; attractiveness to pests for ingestion; ease of killing and fixing without damage to the toxin; and the like. Other considerations include ease of formulation and handling, economics, storage stability, and the like.

Host organisms of particular interest include yeast, such as Rhodotorula sp., Aureobasidium sp., Saccharomyces sp., and Sporobolomyces sp.; phylloplane organisms such as Pseudomonas sp., Erwinia sp. and Flavobacterium sp.; or such other organisms as Escherichia, Lactobacillus sp., Bacillus sp., and the like. Specific organisms include *Pseudomonas aeruginosa, Pseudomonas fluorescens, Saccharomyces cerevisiae, Bacillus thuringiensis, Escherichia coli, Bacillus subtilis,* and the like.

The cell will usually be intact and be substantially in the proliferative form when treated, rather than in a spore form, although in some instances spores may be employed.

Treatment of the microbial cell, e.g., a microbe containing the B.t. toxin gene, can be by chemical or physical means, or by a combination of chemical and/or physical means, so long as the technique does not deleteriously affect the properties of the toxin, nor diminish the cellular capability in protecting the toxin. Examples of chemical reagents are halogenating agents, particularly halogens of atomic no. 17-80. More particularly, iodine can be used under mild conditions and for sufficient time to achieve the desired results. Other suitable techniques include treatment with aldehydes, such as formaldehyde and glutaraldehyde; anti-infectives, such as zephiran chloride and cetylpyridinium chloride; alcohols, such as isopropyl and ethanol; various histologic fixatives, such as Bouin's fixative and Helly's fixative (See: Humason, Gretchen L., Animal Tissue Techniques, W. H. Freeman and Company, 1967); or a combination of physical (heat) and chemical agents that preserve and prolong the activity of the toxin produced in the cell when the cell is administered to the host animal. Examples of physical means are short wavelength radiation such as gamma-radiation and X-radiation, freezing, UV irradiation, lyophilization, and the like.

The cells generally will have enhanced structural stability which will enhance resistance to environmental conditions. Where the pesticide is in a proform, the method of inactivation should be selected so as not to inhibit processing of the proform to the mature form of the pesticide by the target pest pathogen. For example, formaldehyde will crosslink proteins and could inhibit processing of the proform of a polypeptide pesticide. The method of inactivation or killing retains at least a substantial portion of the bio-availability or bioactivity of the toxin.

The cellular host containing the B.t. insecticidal gene may be grown in any convenient nutrient medium, where the DNA construct provides a selective advantage, providing for a selective medium so that substantially all or all of the cells retain the B.t. gene. These calls may then be harvested in accordance with conventional ways. Alternatively, the cells can be treated prior to harvesting.

The B.t. cells may be formulated in a variety of ways. They may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

The pesticidal concentration will vary widely depending upon the nature of the particular formulation, particularly whether it is a concentrate or to be used directly. The pesticide will be present in at least 1% by weight and may be 100% by weight. The dry formulations will have from about 1–95% by weight of the pesticide while the liquid formulations will generally be from about 1–60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the coleopteran pest(s), e.g., plants, soil or water, by spraying, dusting, sprinkling, or the like.

Following are examples which illustrate procedures, including the best mode, for practicing the invention. These examples should not be construed as limiting. All percentages are by weight and all solvent mixture proportions are by volume unless otherwise noted.

EXAMPLE 1

Cloning of Novel Toxin Gene and Transformation into *Bacillus megaterium*

Total cellular DNA was prepared by growing the cells of B.t. isolate 43F and B.t.s.d. to a low optical density ($OD_{600}$=1.0) and recovering the cells by centrifugation. The cells were protoplasted in a buffer containing 20% sucrose and 50 mg/ml lysozyme. The protoplasts were lysed by addition of SDS to a final concentration of 4%. The cellular material was precipitated overnight at 4° C. in 100 mM neutral potassium chloride. The supernate was phenol/chloroform extracted twice and the DNA precipitated in 68% ethanol. The DNA was purified on a cesium chloride gradient. DNA's from strains 43F and B.t.s.d. (as a standard of reference) were digested with EcoRI and run out on a 0.8% agarose gel. The gel was Southern blotted and probed with the nick translated ORF XmnI to PstI fragment of the toxin encoding gene isolated from B.t.s.d. (this will be subsequently referred to as probe). The results showed 43F to hybridize to probe at 7.5 Kb which is different than the standard.

Preparative amounts of 43F DNA were digested with EcoRI and run out on a 0.8% agarose gel. The 7.5 Kb region of the preparative gel was isolated and the DNA electroeluted and concentrated using an ELUTIP™-d (Schleicher and Schuell, Keene, N.H.) ion exchange column. A sample was blotted and probed to verify the fragment was indeed isolated. The 7.5 Kb EcoRI fragment was ligated to Lambda ZAP™ EcoRI arms. The packaged recombinant phage were plated out with *E. coli* strain BB4 (Stratagene Cloning Systems, La Jolla, Calif.) to give high plaque density.

The plaques were screened by standard procedures with probe. The plaques that hybridized were purified and rescreened at a lower plaque density. The resulting phage were grown with M13 helper phage (Stratagene) and the recombinant BLUESCRIPT™ plasmid was automatically excised and packaged. The "phagemid" was re-infected in XL1-blue *E. coli* cells (Stratagene) as part cf the automatic excision process. The infected XL1-blue cells were screened for ampicillin resistance and the resulting colonies were miniprepped to find the desired plasmid pM1,98-4. The recombinant *E. coli* XL1-Blue (pM1,98-4) strain is called MR381.

The plasmid pM1,98-4 contained a 7.5 Kb EcoRI insert. To verify that this insert was the one of interest, a Southern blot was performed and probed. The 7.5 Kb band hybridized with the probe, confirming that the fragment had been cloned. Restriction endonuclease analysis of the 7.5 Kb EcoRI fragment with the enzymes HindIII, PstI, SpeI, BamHI and XbaI was done to show that a coleopteran gene different than B.t.s.d. had been cloned. The enzymes which cut inside the 7.5 Kb EcoRI fragment were HindIII (twice) SpeI (twice) and PstI (once). The ORF of the 43F gene cuts once with HindIII, twice with SpeI and does not cut with XbaI, EcoRI, or BamHI. In comparison to the coleopteran-active gene already cloned and sequenced, the 7.5 Kb EcoRI fragment shows no similarity in its restriction map. Sequence data shows an open reading frame of 1963 bp with at best 70% homology to the toxin encoding gene of B.t.sd. The recombinant BLUESCRIPT™ plasmid has been fused with the Bacillus plasmid pBC16-1SpeI and transformed into *B. megaterium* for expression by the following procedure. The plasmid pM1,98-4 was completely digested with XbaI. The Bacillus vector pBC16-1, received from the Bacillus Genetic Stock Center (Ohio State University), was terminally digested with EcoRI and then made blunt-ended by filling the 5' overhang using the Klenow fragment and deoxnucleotide triphosphates. SpeI linker was added and the resulting plasmid was called pBC16-1SpeI. This plasmid was terminally digested with SpeI. The XbaI overhang of pM1,98-4 (XbaI linear) and the SpeI overhang of pBC16-1SpeI (SpeI linear) are complementary. The two were fused together with T4 DNA Ligase and transformad into competent *E. coli* cells DH5 (BRL). Screening of tetracycline-resistant colonies produced the desired plasmid called pM2,18-1. This plasmid was then transformed, using standard procedures, into *B. megatarium. B. megatarium* (pM2,18-1) was grown to sporulation producing crystal inclusions. Polyacrylamide gel analysis of a spore crystal preparation suggests that an approximately 70 Kd molecular weight protein is being produced. This is in agreement with the molecular mass of 74.228 Kd predicted from the amino acid sequence as deduced from the nucleotide sequence. The novel gene of the invention has homology to the B.t.s.d. toxin gene but is clearly distinguished from the B.t.s.d. gene by a unique nucleotide sequence.

Data from standard insect tests show that the novel toxin of the invention is active against *Leptinotarsa texana,* a surrogate test species for the Colorado Potato Beetle (CPB). Novel B.t. isolate 43F has been shown to be active against *L. texana* and CPB.

The above cloning procedures were conducted using standard procedures unless otherwise noted.

The various methods employed in the preparation of the plasmids and transformation of host organisms are well known in the art. These procedures are all described in Maniatis, T., Fritsch, E. F., and Sambrook, J. (1982) *Molecular Cloning: A Laboratory Manual,* Cold Spring Harbor Laboratory, New York. Thus, it is within the skill of those in the genetic engineering art to extract DNA from microbial cells, perform restriction enzyme digestions, electrophorese DNA fragments, tail and anneal plasmid and insert DNA, ligate DNA, transform cells, prepare plasmid DNA, electrophorese proteins, and sequence DNA.

The restriction enzymes disclosed herein can be purchased from Bethesda Research Laboratories, Gaithersburg, Md., or New England Biolabs, Beverly, Mass. The enzymes are used according to the instructions provided by the supplier.

Plasmid pM1,98-4 containing the B.t. toxin gene, can be removed from the transformed host microbe by use of standard well-known procedures. For example, *E. coli* XL1-Blue (pM1,98-4) can be subjected to cleared lysate isopycnic density gradient procedures, and the like, to recover pM1,98-4.

EXAMPLE 2

Insertion of Toxin Gene Into Plants

The novel gene coding for the novel insecticidal toxin, as disclosed herein, can be inserted into plant cells using the Ti plasmid from *Agrobacter tumefaciens.* Plant cells can then be caused to regenerate into plants (Zambryski, P., Joos, H., Gentello, C., Leemans, J., Van Montague, M. and Schell, J [1983] Cell 32:1033-1043). A particularly useful vector in this regard is pEND4K (Klee, H. J., Yanofsky, M. F. and Nester, E. W. [1985] Bio/Technology 3:637-642). This plasmid can replicate both in plant cells and in bacteria and has multiple cloning sites for passenger genes. The toxin gene, for example, can be inserted into the BamHI site of pEND4K, propagated in *E. coli,* and transformed into appropriate plant cells.

EXAMPLE 3

Cloning of Novel *B. thuringiensis* Gene Into Baculoviruses

The novel gene of the invention can be cloned into baculoviruses such as *Autographa californica* nuclear polyhedrosis virus (AcNPV). Plasmids can be constructed that contain the AcNPV genome cloned into a commercial cloning vector such as pUC8. The AcNPV genome is modified so that the coding region of the polyhedrin gene is removed and a unique cloning site for a passenger gene is placed directly behind the polyhedrin promoter. Examples of such vectors are pGP-B6874, described by Pennock et al. (Pennock, G. D., Shoemaker, C. and Miller, L. K. [1984] Mol. Cell. Biol. 4:399-406), and pAC380, described by Smith et al. (Smith, G. E., Summers, M. D. and Fraser, M. J. [1983] Mol Cell. Biol. 3:2156-2165). The gene coding for the novel protein toxin of the invention can be modified with BamHI linkers at appropriate regions both upstream and downstream from the coding region and inserted into the passenger site of one of the AcNPV vectors.

As disclosed previously, the nucleotide sequence encoding the novel B.t. toxin gene is shown in Table 1. The deduced amino acid sequence is shown in Table 2.

It is well known in the art that the amino acid sequence of a protein is determined b1, the nucleotide sequence of the DNA. Because of the redundancy of the genetic code, i.e., more than one coding nucleotide triplet (codon) can be used for most of the amino acids used to make proteins, different nucleotide sequences can code for a particular amino acid. Thus, the genetic code can be depicted as follows:

| | | | |
|---|---|---|---|
| Phenylalanine (Phe) | TTK | Histidine (His) | CAK |
| Leucine (Leu) | XTY | Glutamine (Gln) | CAJ |
| Isoleucine (Ile) | ATM | Asparagine (Asn) | AAK |
| Methionine (Met) | ATG | Lysine (Lys) | AAJ |
| Valine (Val) | GTL | Aspartic acid (Asp) | GAK |
| Serine (Ser) | QRS | Glutamic acid (Glu) | GAJ |
| Proline (Pro) | CCL | Cysteine (Cys) | TGK |
| Threonine (Thr) | ACL | Tryptophan (Trp) | TGG |
| Alanine (Ala) | GCL | Arginine (Arg) | WGZ |
| Tyrosine (Tyr) | TAK | Glycine (Gly) | GGL |
| Termination signal | TAJ | | |

Key: Each 3-letter deoxynucleotide triplet corresponds to a trinucleotide of mRNA, having a 5'-end on the left and a 3'-end on the right. All DNA sequences given herein are those of the strand whose sequence correspond to the mRNA sequence, with thymine substituted for uracil. The letters stand for the purine or pyrimidine bases forming the deoxynucleotide sequence.

A = adenine
G = guanine
C = cytosine
T = thymine
X = T or C if Y is A or G
X = C if Y is C or T
Y = A, G, C or T if X is C
Y = A or G if X is T
W = C or A if Z is A or G
W — C if Z is C or T
Z = A, G, C or T if W is C
Z = A or G if W is A
QR = TC if S is A, G, C or T; alternatively
QR = AG if S is T or C
J = A or G
K = T or C
L = A, T, C or G
M = A, C or T The above shows that the novel amino acid sequence of the B.t. toxin can be prepared by equivalent nucleotide sequences encoding the same amino acid sequence of the protein. Accordingly, the subject invention includes such equivalent nucleotide sequences. In addition it has been shown that proteins of identified structure and function may be constructed by changing the amino acid sequence if such changes do not alter the protein secondary structure (Kaiser, E. T. and Kezdy, F. J. [1984] Science 223:249-255). Thus, the subject invention includes mutants of the amino acid sequence depicted herein which do not alter the protein secondary structure, or if the structure is altered, the biological activity is retained to some degree.

TABLE 1

Nucleotide sequence of novel toxin encoding gene. The ORF starts as marked with the arrow.

| | | | | | | |
|---|---|---|---|---|---|---|
| | 10 | 20 | Met 30 | 40 | 50 | 60 |
| 1 | ATGATAAGAA | TGGGAGGAAG | → AAAAATGAAT | CCAAACAATC | GAAGTGAATA | TGATACGATA |
| 61 | AAGGTTACAC | CTAACAGTGA | ATTGCCAACT | AACCATAATC | AATATCCTTT | AGCTGACAAT |
| 121 | CCAAATTCGA | CACTAGAAGA | ATTAAATTAT | AAAGAATTTT | TAAGAATGAC | TGCAGACAAT |
| 181 | TCTACGGAAG | TGCTAGACAG | CTCTACAGTA | AAAGATGCAG | TTGGGACAGG | AATTTCTGTT |
| 241 | GTAGGACAGA | TTTTAGGTGT | TGTAGGGGTT | CCATTTGCTG | GGGCGCTCAC | TTCATTTTAT |
| | 310 | 320 | 330 | 340 | 350 | 360 |
| 301 | CAATCATTTC | TTAACGCTAT | ATGGCCAAGT | GATGCTGACC | CATGGAAGGC | TTTTATGGCA |
| 361 | CAAGTGGAAG | TACTGATAGA | TAAGAAAATA | GAGGAGTATG | CTAAAAGTAA | AGCTCTTGCA |
| 421 | GAGTTACAGG | GTCTTCAAAA | TAATTTTGAA | GATTATGTAA | ATGCGTTGGA | TTCCTGGAAG |
| 481 | AAAGCGCCTG | TAAATTTACG | AAGTCGAAGA | AGCCAAGATC | GAATAAGAGA | ACTTTTTTCT |
| 541 | CAAGCAGAAA | GCCATTTTCG | TAATTCCATG | CCGTCATTTG | CGGTTTCCAA | ATTCGAAGTT |
| | 610 | 620 | 630 | 640 | 650 | 660 |

TABLE 1-continued

Nucleotide sequence of novel toxin encoding gene. The ORF starts as marked with the arrow.

| | | | | | | |
|---|---|---|---|---|---|---|
| 601 | CTGTTTCTAC | CAACATATGC | ACAAGCTGCA | AATACACATT | TATTGCTATT | AAAAGATGCT |
| 661 | CAAGTTTTTG | GAGAAGAATG | GGGATATTCT | TCAGAAGATA | TTGCTGAATT | TTATCAAAGA |
| 721 | CAATTAAAAC | TTACGCAACA | ATACACTGAC | CATTGTGTCA | ATTGGTATAA | TGTTGGATTA |
| 781 | AATAGTTTAA | GAGGTTCAAC | TTATGATGCA | TGGGTCAAAT | TTAACCGTTT | TCGCAGAGAA |
| 841 | ATGACATTAA | CTGTATTAGA | TCTAATTGTA | TTATTCCCAT | TTTATGATGT | TCGGTTATAC |
| | 910 | 920 | 930 | 940 | 950 | 960 |
| 901 | TCAAAAGGAG | TTAAAACAGA | ACTAACAAGA | GACATTTTTA | CAGATCCAAT | TTTTACACTC |
| 961 | AATGCTCTTC | AAGAGTATGG | ACCAACTTTT | TCGAGTATAG | AAAACTCTAT | TCGAAAACCT |
| 1021 | CATTTATTTG | ATTATTTGCG | TGGGATTGAA | TTTCATACGC | GTCTTCGACC | TGGTTACTCT |
| 1081 | GGGAAAGATT | CTTTCAATTA | TTGGTCTGGT | AATTATGTAG | AAACTAGACC | TAGTATAGGA |
| 1141 | TCTAATGATA | CAATCACTTC | CCCATTTTAT | GGAGATAAAT | CTATTGAACC | TATACAAAAG |
| | 1210 | 1220 | 1230 | 1240 | 1250 | 1260 |
| 1201 | CTAAGCTTTG | ATGGACAAAA | AGTTTATCGA | ACTATAGCTA | ATACAGACAT | AGCGGCTTTT |
| 1261 | CCGGATGGCA | AGATATATTT | TGGTGTTACG | AAAGTTGATT | TTAGTCAATA | TGATGATCAA |
| 1321 | AAAAATGAAA | CTAGTACACA | AACATATGAT | TCAAAAAGAT | ACAATGGCTA | TTTAGGTGCA |
| 1381 | CAGGATTCTA | TCGACCAATT | ACCACCAGAA | ACAACAGATG | AACCACTTGA | AAAAGCATAT |
| 1441 | AGTCATCAGC | TTAATTACGC | AGAATGTTTC | TTAATGCAGG | ACCGTCGTGG | AACAATTCCA |
| | 1510 | 1520 | 1530 | 1540 | 1550 | 1560 |
| 1501 | TTTTTTACTT | GGACACATAG | AAGTGTAGAC | TTTTTTAATA | CAATTGATGC | TGAAAAAATT |
| 1561 | ACTCAACTTC | CAGTAGTGAA | AGCATATGCC | TTGTCTTCAG | GCGCTTCCAT | TATTGAAGGT |
| 1621 | CCAGGATTCA | CAGGAGGAAA | TTTACTATTC | CTAAAAGAAT | CTAGTAATTC | AATTGCTAAA |
| 1681 | TTTAAAGTTA | CCTTAAATTC | AGCAGCCTTG | TTACAACGAT | ATCGCGTAAG | AATACGCTAT |
| 1741 | GCTTCAACCA | CTAACCTACG | ACTTTTCGTG | CAAAATTCAA | ACAATGATTT | TCTTGTCATC |
| | 1810 | 1820 | 1830 | 1840 | 1850 | 1860 |
| 1801 | TACATTAATA | AAACTATGAA | TATAGATGGT | GATTTAACAT | ATCAAACATT | TGATTTCGCA |
| 1861 | ACTAGTAATT | CTAATATGGG | ATTCTCTGGT | GATACAAATG | ACTTTATAAT | AGGAGCAGAA |
| 1921 | TCTTTCGTTT | CTAATGAAAA | AATCTATATA | GATAAGATAG | AATTTATCCC | AGTACAA* |

TABLE 2

Deduced amino acid sequence of novel toxin.

| | | | | | | | | | | | | | | | |
|---|---|---|---|---|---|---|---|---|---|---|---|---|---|---|---|
| | | | | | 5 | | | | | 10 | | | | | 15 |
| 1 | Met | Asn | Pro | Asn | Asn | Arg | Ser | Glu | Tyr | Asp | Thr | Ile | Lys | Val | Thr |
| 16 | Pro | Asn | Ser | Glu | Leu | Pro | Thr | Asn | His | Asn | Gln | Tyr | Pro | Leu | Ala |
| 31 | Asp | Asn | Pro | Asn | Ser | Thr | Leu | Glu | Glu | Leu | Asn | Tyr | Lys | Glu | Phe |
| 46 | Leu | Arg | Met | Thr | Ala | Asp | Asn | Ser | Thr | Glu | Val | Leu | Asp | Ser | Ser |
| 61 | Thr | Val | Lys | Asp | Ala | Val | Gly | Thr | Gly | Ile | Ser | Val | Val | Gly | Gln |
| 76 | Ile | Leu | Gly | Val | Val | Gly | Val | Pro | Phe | Ala | Gly | Ala | Leu | Thr | Ser |
| 91 | Phe | Tyr | Gln | Ser | Phe | Leu | Asn | Ala | Ile | Trp | Pro | Ser | Asp | Ala | Asp |
| 106 | Pro | Trp | Lys | Ala | Phe | Met | Ala | Gln | Val | Glu | Val | Leu | Ile | Asp | Lys |
| 121 | Lys | Ile | Glu | Glu | Tyr | Ala | Lys | Ser | Lys | Ala | Leu | Ala | Glu | Leu | Gln |
| 136 | Gly | Leu | Gln | Asn | Asn | Phe | Glu | Asp | Tyr | Val | Asn | Ala | Leu | Asp | Ser |
| 151 | Trp | Lys | Lys | Ala | Pro | Val | Asn | Leu | Arg | Ser | Arg | Arg | Ser | Gln | Asp |
| 166 | Arg | Ile | Arg | Glu | Leu | Phe | Ser | Gln | Ala | Glu | Ser | His | Phe | Arg | Asn |
| 181 | Ser | Met | Pro | Ser | Phe | Ala | Val | Ser | Lys | Phe | Glu | Val | Leu | Phe | Leu |
| 196 | Pro | Thr | Tyr | Ala | Gln | Ala | Ala | Asn | Thr | His | Leu | Leu | Leu | Leu | Lys |
| 211 | Asp | Ala | Gln | Val | Phe | Gly | Glu | Glu | Trp | Gly | Tyr | Ser | Ser | Glu | Asp |
| 226 | Ile | Ala | Glu | Phe | Tyr | Gln | Arg | Gln | Leu | Lys | Leu | Thr | Gln | Gln | Tyr |
| 241 | Thr | Asp | His | Cys | Val | Asn | Trp | Tyr | Asn | Val | Gly | Leu | Asn | Ser | Leu |
| 256 | Arg | Gly | Ser | Thr | Tyr | Asp | Ala | Trp | Val | Lys | Phe | Asn | Arg | Phe | Arg |
| 271 | Arg | Glu | Met | Thr | Leu | Thr | Val | Leu | Asp | Leu | Ile | Val | Leu | Phe | Pro |
| 286 | Phe | Tyr | Asp | Val | Arg | Leu | Tyr | Ser | Lys | Gly | Val | Lys | Thr | Glu | Leu |
| 301 | Thr | Arg | Asp | Ile | Phe | Thr | Asp | Pro | Ile | Phe | Thr | Leu | Asn | Ala | Leu |
| 316 | Gln | Glu | Tyr | Gly | Pro | Thr | Phe | Ser | Ser | Ile | Glu | Asn | Ser | Ile | Arg |
| 331 | Lys | Pro | His | Leu | Phe | Asp | Tyr | Leu | Arg | Gly | Ile | Glu | Phe | His | Thr |
| 346 | Arg | Leu | Arg | Pro | Gly | Tyr | Ser | Gly | Lys | Asp | Ser | Phe | Asn | Tyr | Trp |
| 361 | Ser | Gly | Asn | Tyr | Val | Glu | Thr | Arg | Pro | Ser | Ile | Gly | Ser | Asn | Asp |
| 376 | Thr | Ile | Thr | Ser | Pro | Phe | Tyr | Gly | Asp | Lys | Ser | Ile | Glu | Pro | Ile |
| 391 | Gln | Lys | Leu | Ser | Phe | Asp | Gly | Gln | Lys | Val | Tyr | Arg | Thr | Ile | Ala |
| 406 | Asn | Thr | Asp | Ile | Ala | Ala | Phe | Pro | Asp | Gly | Lys | Ile | Tyr | Phe | Gly |
| 421 | Val | Thr | Lys | Val | Asp | Phe | Ser | Gln | Tyr | Asp | Asp | Gln | Lys | Asn | Glu |
| 436 | Thr | Ser | Thr | Gln | Thr | Tyr | Asp | Ser | Lys | Arg | Tyr | Asn | Gly | Tyr | Leu |
| 451 | Gly | Ala | Gln | Asp | Ser | Ile | Asp | Gln | Leu | Pro | Pro | Glu | Thr | Thr | Asp |
| 466 | Glu | Pro | Leu | Glu | Lys | Ala | Tyr | Ser | His | Gln | Leu | Asn | Tyr | Ala | Glu |
| 481 | Cys | Phe | Leu | Met | Gln | Asp | Arg | Arg | Gly | Thr | Ile | Pro | Phe | Phe | Thr |
| 496 | Trp | Thr | His | Arg | Ser | Val | Asp | Phe | Phe | Asn | Thr | Ile | Asp | Ala | Glu |
| 511 | Lys | Ile | Thr | Gln | Leu | Pro | Val | Val | Lys | Ala | Tyr | Ala | Leu | Ser | Ser |
| 526 | Gly | Ala | Ser | Ile | Ile | Glu | Gly | Pro | Gly | Phe | Thr | Gly | Gly | Asn | Leu |
| 541 | Leu | Phe | Leu | Lys | Glu | Ser | Ser | Asn | Ser | Ile | Ala | Lys | Phe | Lys | Val |
| 556 | Thr | Leu | Asn | Ser | Ala | Ala | Leu | Leu | Gln | Arg | Tyr | Arg | Val | Arg | Ile |
| 571 | Arg | Tyr | Ala | Ser | Thr | Thr | Asn | Leu | Arg | Leu | Phe | Val | Gln | Asn | Ser |
| 586 | Asn | Asn | Asp | Phe | Leu | Val | Ile | Tyr | Ile | Asn | Lys | Thr | Met | Asn | Ile |
| 601 | Asp | Gly | Asp | Leu | Thr | Tyr | Gln | Thr | Phe | Asp | Phe | Ala | Thr | Ser | Asn |
| 616 | Ser | Asn | Met | Gly | Phe | Ser | Gly | Asp | Thr | Asn | Asp | Phe | Ile | Ile | Gly |
| 631 | Ala | Glu | Ser | Phe | Val | Ser | Asn | Glu | Lys | Ile | Tyr | Ile | Asp | Lys | Ile |
| 646 | Glu | Phe | Ile | Pro | Val | Gln | | | | | | | | | |

TABLE 3

| | | | | 5 | | | | Start | 10 | | | | | 15 | | | | | 20 |
|---|---|---|---|---|---|---|---|---|---|---|---|---|---|---|---|---|---|---|---|
| Met | Ile | Arg | Met | Gly | Gly | Arg | Lys | → Met | Asn | Pro | Asn | Asn | Arg | Ser | Glu | Tyr | Asp | Thr | Ile |
| ATG | ATA | AGA | ATG | GGA | GGA | AGA | AAA | ATG | AAT | CCA | AAC | AAT | CGA | AGT | GAA | TAT | GAT | ACG | ATA |
| | | | | 25 | | | | | 30 | | | | | 35 | | | | | 40 |
| Lys | Val | Thr | Pro | Asn | Ser | Glu | Leu | Pro | Thr | Asn | His | Asn | Gln | Tyr | Pro | Leu | Ala | Asp | Asn |
| AAG | GTT | ACA | CCT | AAC | AGT | GAA | TTC | CCA | ACT | AAC | CAT | AAT | CAA | TAT | CCT | TTA | GCT | GAC | AAT |
| | | | | 45 | | | | | 50 | | | | | 55 | | | | | 60 |
| Pro | Asn | Ser | Thr | Leu | Glu | Glu | Leu | Asn | Tyr | Lys | Glu | Phe | Leu | Arg | Met | Thr | Ala | Asp | Asn |
| CCA | AAT | TCG | ACA | CTA | GAA | GAA | TTA | AAT | TAT | AAA | GAA | TTT | TTA | AGA | ATG | ACT | GCA | GAC | AAT |
| | | | | 65 | | | | | 70 | | | | | 75 | | | | | 80 |
| Ser | Thr | Glu | Val | Leu | Asp | Ser | Ser | Thr | Val | Lys | Asp | Ala | Val | Gly | Thr | Gly | Ile | Ser | Val |
| TCT | ACG | GAA | GTG | CTA | GAC | AGC | TCT | ACA | GTA | AAA | GAT | GCA | GTT | GGG | ACA | GGA | ATT | TCT | GTT |
| | | | | 85 | | | | | 90 | | | | | 95 | | | | | 100 |
| Val | Gly | Gln | Ile | Leu | Gly | Val | Val | Gly | Val | Pro | Phe | Ala | Gly | Ala | Leu | Thr | Ser | Phe | Tyr |
| GTA | GGA | CAG | ATT | TTA | GGT | GTT | GTA | GGG | GTT | CCA | TTT | GCT | GGG | GCG | CTC | ACT | TCA | TTT | TAT |
| | | | | 105 | | | | | 110 | | | | | 115 | | | | | 120 |
| Gln | Ser | Phe | Leu | Asn | Ala | Ile | Trp | Pro | Ser | Asp | Ala | Asp | Pro | Trp | Lys | Ala | Phe | Met | Ala |
| CAA | TCA | TTT | CTT | AAC | GCT | ATA | TGG | CCA | AGT | GAT | GCT | GAC | CCA | TGG | AAG | GCT | TTT | ATG | GCA |
| | | | | 125 | | | | | 130 | | | | | 135 | | | | | 140 |
| Gln | Val | Glu | Val | Leu | Ile | Asp | Lys | Lys | Ile | Glu | Glu | Tyr | Ala | Lys | Ser | Lys | Ala | Leu | Ala |
| CAA | GTG | GAA | GTA | CTG | ATA | GAT | AAG | AAA | ATA | GAG | GAG | TAT | GCT | AAA | AGT | AAA | GCT | CTT | GCA |
| | | | | 145 | | | | | 150 | | | | | 155 | | | | | 160 |
| Glu | Leu | Gln | Gly | Leu | Gln | Asn | Asn | Phe | Glu | Asp | Tyr | Val | Asn | Ala | Leu | Asp | Ser | Trp | Lys |
| GAG | TTA | CAG | GGT | CTT | CAA | AAT | AAT | TTT | GAA | GAT | TAT | GTA | AAT | GCG | TTG | GAT | TCC | TGG | AAG |
| | | | | 165 | | | | | 170 | | | | | 175 | | | | | 180 |
| Lys | Ala | Pro | Val | Asn | Leu | Arg | Ser | Arg | Arg | Ser | Gln | Asp | Arg | Ile | Arg | Glu | Leu | Phe | Ser |
| AAA | GCG | CCT | GTA | AAT | TTA | CGA | AGT | CGA | AGA | AGC | CAA | GAT | CGA | ATA | AGA | GAA | CTT | TTT | TCT |
| | | | | 185 | | | | | 190 | | | | | 195 | | | | | 200 |
| Gln | Ala | Glu | Ser | His | Phe | Arg | Asn | Ser | Met | Pro | Ser | Phe | Ala | Val | Ser | Lys | Phe | Glu | Val |
| CAA | GCA | GAA | AGC | CAT | TTT | CGT | AAT | TCC | ATG | CCG | TCA | TTT | GCG | GTT | TCC | AAA | TTC | GAA | GTT |
| | | | | 205 | | | | | 210 | | | | | 215 | | | | | 220 |
| Leu | Phe | Leu | Pro | Thr | Tyr | Ala | Gln | Ala | Ala | Asn | Thr | His | Leu | Leu | Leu | Leu | Lys | Asp | Ala |
| CTG | TTT | CTA | CCA | ACA | TAT | GCA | CAA | GCT | GCA | AAT | ACA | CAT | TTA | TTG | CTA | TTA | AAA | GAT | GCT |
| | | | | 225 | | | | | 230 | | | | | 235 | | | | | 240 |
| Gln | Val | Phe | Gly | Glu | Glu | Trp | Gly | Tyr | Ser | Ser | Glu | Asp | Ile | Ala | Glu | Phe | Tyr | Gln | Arg |
| CAA | GTT | TTT | GGA | GAA | GAA | TGG | GGA | TAT | TCT | TCA | GAA | GAT | ATT | GCT | GAA | TTT | TAT | CAA | AGA |
| | | | | 245 | | | | | 250 | | | | | 255 | | | | | 260 |
| Gln | Leu | Lys | Leu | Thr | Gln | Gln | Tyr | Thr | Asp | His | Cys | Val | Asn | Trp | Tyr | Asn | Val | Gly | Leu |
| CAA | TTA | AAA | CTT | ACG | CAA | CAA | TAC | ACT | GAC | CAT | TGT | GTC | AAT | TGG | TAT | AAT | GTT | GGA | TTA |
| | | | | 265 | | | | | 270 | | | | | 275 | | | | | 280 |
| Asn | Ser | Leu | Arg | Gly | Ser | Thr | Tyr | Asp | Ala | Trp | Val | Lys | Phe | Asn | Arg | Phe | Arg | Arg | Glu |
| AAT | AGT | TTA | AGA | GGT | TCA | ACT | TAT | GAT | GCA | TGG | GTC | AAA | TTT | AAC | CGT | TTT | CGC | AGA | GAA |
| | | | | 285 | | | | | 290 | | | | | 295 | | | | | 300 |
| Met | Thr | Leu | Thr | Val | Leu | Asp | Leu | Ile | Val | Leu | Phe | Pro | Phe | Tyr | Asp | Val | Arg | Leu | Tyr |
| ATG | ACA | TTA | ACT | GTA | TTA | GAT | CTA | ATT | GTA | TTA | TTC | CCA | TTT | TAT | GAT | GTT | CGG | TTA | TAC |
| | | | | 305 | | | | | 310 | | | | | 315 | | | | | 320 |
| Ser | Lys | Gly | Val | Lys | Thr | Glu | Leu | Thr | Arg | Asp | Ile | Phe | Thr | Asp | Pro | Ile | Phe | Thr | Leu |
| TCA | AAA | GGA | GTT | AAA | ACA | GAA | CTA | ACA | AGA | GAC | ATT | TTT | ACA | GAT | CCA | ATT | TTT | ACA | CTC |
| | | | | 325 | | | | | 330 | | | | | 335 | | | | | 340 |
| Asn | Ala | Leu | Gln | Glu | Tyr | Gly | Pro | Thr | Phe | Ser | Ser | Ile | Glu | Asn | Ser | Ile | Arg | Lys | Pro |
| AAT | GCT | CTT | CAA | GAG | TAT | GGA | CCA | ACT | TTT | TCG | AGT | ATA | GAA | AAC | TCT | ATT | CGA | AAA | CCT |
| | | | | 345 | | | | | 350 | | | | | 355 | | | | | 360 |
| His | Leu | Phe | Asp | Tyr | Leu | Arg | Gly | Ile | Glu | Phe | His | Thr | Arg | Leu | Arg | Pro | Gly | Tyr | Ser |

TABLE 3-continued

| | | | | | | | | | | | | | | | | | | | |
|---|---|---|---|---|---|---|---|---|---|---|---|---|---|---|---|---|---|---|---|
| CAT | TTA | TTT | GAT | TAT | TTG | CGT | GGG | ATT | GAA | TTT | CAT | ACG | CGT | CTT | CGA | CCT | GGT | TAC | TCT |
| | | | | 365 | | | | | 370 | | | | | 375 | | | | | 380 |
| Gly | Lys | Asp | Ser | Phe | Asn | Tyr | Trp | Ser | Gly | Asn | Tyr | Val | Glu | Thr | Arg | Pro | Ser | Ile | Gly |
| GGG | AAA | GAT | TCT | TTC | AAT | TAT | TGG | TCT | GGT | AAT | TAT | GTA | GAA | ACT | AGA | CCT | AGT | ATA | GGA |
| | | | | 385 | | | | | 390 | | | | | 395 | | | | | 400 |
| Ser | Asn | Asp | Thr | Ile | Thr | Ser | Pro | Phe | Tyr | Gly | Asp | Lys | Ser | Ile | Glu | Pro | Ile | Gln | Lys |
| TCT | AAT | GAT | ACA | ATC | ACT | TCC | CCA | TTT | TAT | GGA | GAT | AAA | TCT | ATT | GAA | CCT | ATA | CAA | AAG |
| | | | | 405 | | | | | 410 | | | | | 415 | | | | | 420 |
| Leu | Ser | Phe | Asp | Gly | Gln | Lys | Val | Tyr | Arg | Thr | Ile | Ala | Asn | Thr | Asp | Ile | Ala | Ala | Phe |
| CTA | AGC | TTT | GAT | GGA | CAA | AAA | GTT | TAT | CGA | ACT | ATA | GCT | AAT | ACA | GAC | ATA | GCG | GCT | TTT |
| | | | | 425 | | | | | 430 | | | | | 435 | | | | | 440 |
| Pro | Asp | Gly | Lys | Ile | Tyr | Phe | Gly | Val | Thr | Lys | Val | Asp | Phe | Ser | Gln | Tyr | Asp | Asp | Gln |
| CCG | GAT | GGC | AAG | ATA | TAT | TTT | GGT | GTT | ACG | AAA | GTT | GAT | TTT | AGT | CAA | TAT | GAT | GAT | CAA |
| | | | | 445 | | | | | 450 | | | | | 455 | | | | | 460 |
| Lys | Asn | Glu | Thr | Ser | Thr | Gln | Thr | Tyr | Asp | Ser | Lys | Arg | Tyr | Asn | Gly | Tyr | Leu | Gly | Ala |
| AAA | AAT | GAA | ACT | AGT | ACA | CAA | ACA | TAT | GAT | TCA | AAA | AGA | TAC | AAT | GGC | TAT | TTA | GGT | GCA |
| | | | | 465 | | | | | 470 | | | | | 475 | | | | | 480 |
| Gln | Asp | Ser | Ile | Asp | Gln | Leu | Pro | Pro | Glu | Thr | Thr | Asp | Glu | Pro | Leu | Glu | Lys | Ala | Tyr |
| CAG | GAT | TCT | ATC | GAC | CAA | TTA | CCA | CCA | GAA | ACA | ACA | GAT | GAA | CCA | CTT | GAA | AAA | GCA | TAT |
| | | | | 485 | | | | | 490 | | | | | 495 | | | | | 500 |
| Ser | His | Gln | Leu | Asn | Tyr | Ala | Glu | Cys | Phe | Leu | Met | Gln | Asp | Arg | Arg | Gly | Thr | Ile | Pro |
| AGT | CAT | CAG | CTT | AAT | TAC | GCA | GAA | TGT | TTC | TTA | ATG | CAG | GAC | CGT | CGT | GGA | ACA | ATT | CCA |
| | | | | 505 | | | | | 510 | | | | | 515 | | | | | 520 |
| Phe | Phe | Thr | Trp | Thr | His | Arg | Ser | Val | Asp | Phe | Phe | Asn | Thr | Ile | Asp | Ala | Glu | Lys | Ile |
| TTT | TTT | ACT | TGG | ACA | CAT | AGA | AGT | GTA | GAC | TTT | TTT | AAT | ACA | ATT | GAT | GCT | GAA | AAA | ATT |
| | | | | 525 | | | | | 530 | | | | | 535 | | | | | 540 |
| Thr | Gln | Leu | Pro | Val | Val | Lys | Ala | Tyr | Ala | Leu | Ser | Ser | Gly | Ala | Ser | Ile | Ile | Glu | Gly |
| ACT | CAA | CTT | CCA | GTA | GTG | AAA | GCA | TAT | GCC | TTG | TCT | TCA | GGC | GCT | TCC | ATT | ATT | GAA | GGT |
| | | | | 545 | | | | | 550 | | | | | 555 | | | | | 560 |
| Pro | Gly | Phe | Thr | Gly | Gly | Asn | Leu | Leu | Phe | Leu | Lys | Glu | Ser | Ser | Asn | Ser | Ile | Ala | Lys |
| CCA | GGA | TTC | ACA | GGA | GGA | AAT | TTA | CTA | TTC | CTA | AAA | GAA | TCT | AGT | AAT | TCA | ATT | GCT | AAA |
| | | | | 565 | | | | | 570 | | | | | 575 | | | | | 580 |
| Phe | Lys | Val | Thr | Leu | Asn | Ser | Ala | Ala | Leu | Leu | Gln | Arg | Tyr | Arg | Val | Arg | Ile | Arg | Tyr |
| TTT | AAA | GTT | ACC | TTA | AAT | TCA | GCA | GCC | TTG | TTA | CAA | CGA | TAT | CGC | GTA | AGA | ATA | CGC | TAT |
| | | | | 585 | | | | | 590 | | | | | 595 | | | | | 600 |
| Ala | Ser | Thr | Thr | Asn | Leu | Arg | Leu | Phe | Val | Gln | Asn | Ser | Asn | Asn | Asp | Phe | Leu | Val | Ile |
| GCT | TCA | ACC | ACT | AAC | CTA | CGA | CTT | TTC | GTG | CAA | AAT | TCA | AAC | AAT | GAT | TTT | CTT | GTC | ATC |
| | | | | 605 | | | | | 610 | | | | | 615 | | | | | 620 |
| Tyr | Ile | Asn | Lys | Thr | Met | Asn | Ile | Asp | Gly | Asp | Leu | Thr | Tyr | Gln | Thr | Phe | Asp | Phe | Ala |
| TAC | ATT | AAT | AAA | ACT | ATG | AAT | ATA | GAT | GGT | GAT | TTA | ACA | TAT | CAA | ACA | TTT | GAT | TTC | GCA |
| | | | | 625 | | | | | 630 | | | | | 635 | | | | | 640 |
| Thr | Ser | Asn | Ser | Asn | Met | Gly | Phe | Ser | Gly | Asp | Thr | Asn | Asp | Phe | Ile | Ile | Gly | Ala | Glu |
| ACT | AGT | AAT | TCT | AAT | ATG | GGA | TTC | TCT | GGT | GAT | ACA | AAT | GAC | TTT | ATA | ATA | GGA | GCA | GAA |
| | | | | 645 | | | | | 650 | | | | | 655 | | | | | |
| Ser | Phe | Val | Ser | Asn | Glu | Lys | Ile | Tyr | Ile | Asp | Lys | Ile | Glu | Phe | Ile | Pro | Val | Gln | |
| TCT | TTC | GTT | TCT | AAT | GAA | AAA | ATC | TAT | ATA | GAT | AAG | ATA | GAA | TTT | ATC | CCA | GTA | CAA | |

We claim:

1. Essentially pure toxin active against Coleopteran insects having the amino acid sequence shown in FIG. 1.

* * * * *

UNITED STATES PATENT AND TRADEMARK OFFICE

CERTIFICATE OF CORRECTION

PATENT NO. : 5,104,974

DATED : April 14, 1992

INVENTOR(S) : August J. Sick and Thomas E. Gilroy

It is certified that error appears in the above-identified patent and that said Letters Patent is hereby corrected as shown below:

ON THE TITLE PAGE

TITLE: "*Bacillus thuringiensis* Coleopteran-Active Toxin" should read --*Bacillus thuringiensis* Gene Encoding a Coleopteran-Active Toxin--.

Column 4 line 27: "sidercphores" should read --siderophores--.
Column 5 line 43: "Shicella" should read --*Shigella*--.
Column 5 line 46: "Desulfovib rio" should read --Desulfovibrio--.
Column 6 line 55: "calls may" should read --cells may--.
Column 10 line 5: "b1" should be --by--.
Column 10, Table 1,
line 1: " Met 30 AAAAATGAAT" should read -- Met 30 AAAAATGAAT--

UNITED STATES PATENT AND TRADEMARK OFFICE

CERTIFICATE OF CORRECTION

PATENT NO. : 5,104,974

DATED : April 14, 1992

INVENTOR(S) : August J. Sick and Thomas E. Gilroy

It is certified that error appears in the above-indentified patent and that said Letters Patent is hereby corrected as shown below:

Column 13, Table 3, triplet number 28: "TTC" should read --TTG--.

Signed and Sealed this

Eighth Day of June, 1993

Attest:

MICHAEL K. KIRK

*Attesting Officer*

*Acting Commissioner of Patents and Trademarks*